US008877509B2

(12) United States Patent
Dorian et al.

(10) Patent No.: US 8,877,509 B2
(45) Date of Patent: Nov. 4, 2014

(54) SYSTEM AND METHOD FOR ANALYZING SAMPLES LABELED WITH 5, 10, 15, 20 TETRAKIS (4-CARBOXYPHENYL) PORPHINE (TCPP)

(75) Inventors: Constance Dorian, Albuquerque, NM (US); John Cousins, Albuquerque, NM (US); Gordon Bennett, Albuquerque, NM (US)

(73) Assignee: bioAffinity Technologies, Inc., San Antonio, TX (US)

( * ) Notice: Subject to any disclaimer, the term of this patent is extended or adjusted under 35 U.S.C. 154(b) by 22 days.

(21) Appl. No.: 12/839,283

(22) Filed: Jul. 19, 2010

(65) Prior Publication Data

US 2011/0014647 A1    Jan. 20, 2011

Related U.S. Application Data

(60) Provisional application No. 61/226,646, filed on Jul. 17, 2009.

(51) Int. Cl.
| | |
|---|---|
| *G01N 33/48* | (2006.01) |
| *C12Q 1/00* | (2006.01) |
| *G01N 33/574* | (2006.01) |
| *G01N 33/50* | (2006.01) |
| *G01N 33/52* | (2006.01) |
| *G01N 33/58* | (2006.01) |

(52) U.S. Cl.
CPC ...... *G01N 33/5091* (2013.01); *G01N 33/57423* (2013.01); *G01N 33/57492* (2013.01); *G01N 33/52* (2013.01); *G01N 33/582* (2013.01)
USPC .............................................. 436/64; 435/4

(58) Field of Classification Search
None
See application file for complete search history.

(56) References Cited

U.S. PATENT DOCUMENTS

| | | | |
|---|---|---|---|
| 4,485,086 A | 11/1984 | Wong | |
| 4,783,529 A | 11/1988 | Lavallee et al. | |

(Continued)

FOREIGN PATENT DOCUMENTS

| | | |
|---|---|---|
| EP | 2372361 | 10/2011 |
| EP | 1364044 | 1/2012 |

(Continued)

OTHER PUBLICATIONS

"How many species of bacteria are there" (wisegeek.com; accessed Sep. 23, 2011).*

(Continued)

*Primary Examiner* — Bradley L Sisson
(74) *Attorney, Agent, or Firm* — Peacock Myers, P.C.; Janeen Vilven

(57) ABSTRACT

One embodiment of the present invention provides for a method of determining if a sputum sample contains dysplastic or carcinomic cells by obtaining a sputum sample containing cells. The sputum sample is labeled with TCPP to stain cells suspected to be dysplastic or carcinomic. The labeled sputum sample is excited with an excitation wavelength of light of about 475 nm+/−30 nm and emission at about 560 nm+/−30 nm is detected from cells identified to be macrophages. An imager focuses on the plasma membrane of one or more cells suspected to be dysplastic or carcinomic and emission at about 655 nm+/−30 nm, if present, is detected for TCPP labeled cells of the sputum sample after focusing on the plasma membrane of the cells of the sputum sample. Photon flux for each pixel of a sensor is measured to obtain a value for the imaged cell. The measured value is scored to determine if a cell is cancerous or dysplastic.

6 Claims, 9 Drawing Sheets

(56) References Cited

U.S. PATENT DOCUMENTS

| | | | |
|---|---|---|---|
| 4,857,300 A | 8/1989 | Maksem | |
| 4,930,516 A | 6/1990 | Alfano | |
| 5,004,811 A | 4/1991 | Bommer | |
| 5,162,231 A * | 11/1992 | Cole et al. | 436/64 |
| 5,391,547 A | 2/1995 | Cole et al. | |
| 6,190,877 B1 | 2/2001 | Adair | |
| 6,316,215 B1 | 11/2001 | Adair et al. | |
| 6,643,041 B1 | 11/2003 | Ikeda et al. | |
| 6,838,248 B2 * | 1/2005 | Garwin | 435/7.23 |
| 6,984,498 B2 | 1/2006 | Adair | |
| 7,384,764 B2 | 6/2008 | Garwin | |
| 7,670,799 B2 * | 3/2010 | Garwin | 435/40.5 |
| 7,960,138 B2 | 6/2011 | Garwin | |
| 8,486,656 B2 | 7/2013 | Garwin | |
| 2002/0115121 A1 | 8/2002 | Garwin | |
| 2004/0202612 A1 | 10/2004 | Adair | |
| 2005/0079561 A1 | 4/2005 | Garwin | |
| 2005/0233410 A1 | 10/2005 | Garwin | |
| 2006/0058683 A1 | 3/2006 | Chance | |
| 2006/0081770 A1 * | 4/2006 | Buchin | 250/214 VT |
| 2007/0172392 A1 | 7/2007 | Sen | |
| 2009/0004690 A1 | 1/2009 | Garwin | |
| 2010/0216169 A1 | 8/2010 | Garwin | |
| 2012/0149057 A1 | 6/2012 | Garwin | |

FOREIGN PATENT DOCUMENTS

| | | |
|---|---|---|
| JP | 08-245480 | 9/1996 |
| JP | 4307070 | 5/2009 |
| WO | 91/19978 | 12/1991 |
| WO | WO-91/19977 | 12/1991 |
| WO | 92/06097 | 4/1992 |
| WO | WO02/42267 | 5/2002 |
| WO | 2011/009137 | 1/2011 |

OTHER PUBLICATIONS

"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
Berns, Michael W. et al., "In Vitro Cellular Effects of Hematoporphyrin Derivative", *Cancer Research* vol. 42, No. 6 1982, 2325-2328.
Boring, Catherine C., "Cancer Statistics", *CA Cancer J Clin* vol. 43, No. 1 1993, 7-26.
Bunseki, Kagaku, "Reversed-Phase Partition Chromatography for Trace Copper (II), Zinc (II), Manganese (II), and Cobaldt (II) Using Tetrakis (4-Carboxyphenyl) Porphine", *The Japan Society for Analytical Chemistry* vol. 35, No. 9 1986, 829-831.
Clarke, Suzanne E. et al., "Aqueous Complexation Equilibria of Meso Tetrakis(4-carboxyphenyl)porphyrine with Violgens", *J of Physical Chemistry* vol. 106, No. 13 2002, 3235-3242.
Cole, D. A. et al., "Copper-67 Labeled Porphyrin Localization in Inflamed Tissue", *Copper Bioavailability and Metabolism* 1990, 259-272.
Cole, D. A. et al., "The Biological Characteristics of a Water Soluble Porphyrin in Rat Lymph Nodes", *Nucl. Med. Biol. Vole. 17*, No. 5 1990, 457-464.
Cortese, Denis A. et al., "Hematoporphyrin Derivative in the Detection and Localization of Radiographically Occult Lung Cancer", *Am. Rev. Respir. Dis.* vol. 126, No. 1 1992, 1087-1088.
Dellinger, M. et al., "Cellular Uptake of Hydroxyethylvinyldeuteroporphyrin and Photoinactivation of Cultivated Human Leukemia (REH6) Cells", *Biological Abstracts, 82:8, 1986*, Philadelphia, PA, US; Abstract No. 75075, Abstract page AB-679 *of Photochem. Photobiol.*, 43:6 1986, 639-648.
Ferguson, Mark K., "Diagnosing and Staging on Non-Small Cell Lung Cancer", *Hematol Oncol Clin N Am* vol. 4, No. 6 1990, 1053-1068.

Firnau, G. et al., "Cu Labeling of Hematoporphyrin Derivative for Non-Invasive In-Vivo Measurement of Tumor Uptake", *Porphyrin Localization and Treatment of Tumors* 1984, 629-636.
Hambright, P. et al., "The Distribution of Various Water Soluble Radioactive Metalloporphyrins in Tumor Bearing Mice", *Bioinorganic Chemistry* vol. 5 1975, 87-92.
Haroske, G. et al., "Frequency and Diagnostic Reliabilty of Subvisual Morphologic Markers for Malignancy in the Cervical Epithelium", *Arch Geschwulstforsch* vol. 58, No. 3 1988, 159-168.
Hirsch, Fred R. et al., "Prevention and Early Detection of Lung Cancer-Clinical Aspects", *Lung Cancer* vol. 17 1997, 163-174.
Hutchinson, Martha L. et al., "Measurement fo Subvisual Changes in Cervical Squamous Metaplastic Cells for Detecting Abnormality", *Anal. Quant. Cytol. Estol.* vol. 14, No. 4 1992, 330-334.
Kato, Harubumi et al., "Early Detection of Lung Cancer by Means of Hematoporphyrin Derivative Fluorescence and Laser Photoradiation", *Clinics in Chest Medicine* vol. 6, No. 2 1985, 237-253.
Mao, Li et al., "Detection of Oncogene Mutations in Sputum Precedes Diagnosis of Lung Cancer", *Cancer Research* vol. 54 1994, 1634-1637.
Mao, Li et al., "Microsatellite Alterations as Clonal Markers for the Detection of Human Cancer", *Proc. Natl. Acad. Sci.* vol. 91 1994, 9871-9875.
Mercer-Smith, Janet A. et al., "The Development of Copper-67-Labeled Porphyrin-Antibody Conjugates", *Targeted Diagnosis and Therapy* vol. 1 1988, 317-352.
Moan, J. et al., "A Change is the Qauntum Yield of Photoinactivation of Cells Observed During Photodynamic Treatment", *Biological Abstracts*, 86:7, 1988, Philadelphia, PA, US; Abstract No. 72079; Abstract p. AB-772 *of Lasers Med. Sci.*, 3:2 1988, 93-98.
Moan, J. et al., "Photosensitizing Efficiencies, Tumor and Cellular Uptake of Different Photosensitizing Drugs Relevant for Photodynamic Therapy of Cancer", *Biological Abstracts*, 85:5, 1988, Philadelphia, PA, US; Abstract No. 49732; Abstract p. AB-723 *of Photochem. Photobiol.*, 46:5 1987, 713-722.
Moan, J. et al., "The Mechanism of Photodynamic Inactivation of Human Cells in Vitro in the Presence of Haematoporphyrin", *Biological Abstracts*, 68:10, 1979, Philadelphia, PA, US; Abstract No. 62117; Abstract p. 6230, *Br J. Cancer*, 39:4 1979, 398-407.
Montag, Anthony G. et al., "Karyometric Features in Nuclei Near Colonic Adenocarcinoma", *Anal. Quant. Cytol. Histol.* vol. 13 1991, 159-167.
Musser, David A. et al., "The Binding of Tumor Localizing Porphyrins to a Fibrin Matrix and Their Effects Following Photoirradiation", *Res. Comm. In Chem. Path. And Pharm.* vol. 28, No. 3 1980, 505-525.
Patel, K. B., "Fluorescing Cells in Sputum After Parenteral HPD", *Porphyrin Localization and Treatment of Tumors* 1984, 521-530.
Pegaz, B. et al., "Effect of the Lipophilicyt on the Phtothrombic Activity of Biodegradable Nanoparticles Loaded with Porphyrin Derivatives", *TNT2004 Segovia Spain* 2004, 1-2.
Roberts, Jeanette C. et al., "Preparation and Characterization of Copper-67 Porphyrin-Antibody Conjugates", *Journal of Immun. Methods* vol. 105 1987, 153-164.
Roby, Tina J. et al., "Discriminant Analysis of Lower Respiratory Tract Components Associated with Cigarette Smoking, Based on Quantitative Sputum Cytology", *Acta Cytol* vol. 34 1990, 147-154.
Roby, Tina J. et al., "Reliability of a Quantitative Interpretation of Sputum Cytology Slides", *Acta Cytol* vol. 34 1990, 140-146.
Schumann, G. B. et al., "Quantitative Sputum Cytologic Findings in 109 Nonsmokers", *Am Rev Respr Dis* vol. 139 1989, 601-603.
Shulok, Janine R. et al., "Subcellular Localization of Hematoporphyrin Derivative in Bladder Tumor Cells in Culture", *Photochem and Photobiol* vol. 51, No. 4 1990, 451-457.
Sidransky, David, "Importance of Chromosome 9p Loss in Human Lung Cancer", *J Natl Cancer Inst* vol. 87 1995, 1201-1202.
Tockman, Melvyn S. et al., "Sensitive and Specific Monoclonal Antibody Recognition of Human Lung Cancer Antigen on Preserved Sputum Cells: A New Approach to Early Lung Cancer Detection", *J Clin Oncol* vol. 11 1988, 1685-1693.
Tockman, Melvyn S., "The Early Detection of Second Primary Lung Cancers by Sputum Immunostaining", *Chest* vol. 106 1994, 385s-390s.

(56) References Cited

OTHER PUBLICATIONS

Wingo, Phyllis A. et al., "Cancer Statistics", *CA Clinical J Clin* vol. 45 1995, 8-30.

Bartocci, C. et al., "A spectrosphotometric investigation on iron(III)protoporphyrin-IX in water/alcohol/pyridine solvent systems", lnorg. Chim. Acta. vol. 37, No. 1, 1979, L473-L476.

Igarashi, Shukuro et al., "Reversed phase-partition mode HPLC for small amounts of copper (II), zinc (II), manganese (II) and cobalt (II) with α, β, γ, δ-tetrakis (4-carboxyphenyl) porphine", Bunseki Kagaku (Analytical Chemistry) vol. 35, No. 9, 1986, 829-831.

Kancherla, K. et al., "Early Lung Cancer Detection using Nucleua. Segmentation based Features", 2013 IEEE Symposium on Computational Intelligence in Bioinformatics and Computational Biology, 2013, 91-95.

Kancherla, K. et al., "Lung Cancer Detection Using Labeled Sputum Sample: Multi Spectrum Approach", Modern Approaches in Applied Intelligence, 2011, 446-458.

Kancherla, K. et al., "Non Intrusive and Extremely Early Detection of Lung Cancer Using TCPP", 2009 Fourth International Multi-Conference on Computing in the Global Information Technology, IEEE Computer Society, 2009, 104-108.

Osaka, Tetsuya et al., "Transmission Electron Microscopic Study on Electroless Plated Nickel-Molybdenum-Phosphorus Alloy Film", Jpn. J. Apple Phys Part 1, vol. 28, Suppl. 28-3, 1989, 229-233.

Rao, Polisetti D. et al., "Rational Syntheses of Porphyrins Bearing up to Four Different Meso Substituents", J. Org. Chem. vol. 65, No. 22, 2000, 7323-7334.

* cited by examiner

SYSTEM AND METHOD FOR ANALYZING SAMPLES LABELED WITH 5, 10, 15, 20 TETRAKIS (4-CARBOXYPHENYL) PORPHINE (TCPP)

CROSS-REFERENCE TO RELATED APPLICATIONS

This application claims priority to and the benefit of the filing of U.S. Provisional patent application Ser. No. 61/226,646 entitled "System and Method for Analyzing Samples Labeled with 5, 10, 15, 20, Tetrakis (4-Carboxyphenyl) Porphine (TCPP)", filed on Jul. 17, 2009, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

INTRODUCTION

Pathologists, who examine disease progression and analyze tissue samples for abnormalities, including cancer, have determined that a cellular condition called dysplasia, which refers to abnormal formation or maturation of cells, can potentially identify cells in a pre-cancerous condition. Unchecked, dysplasia can progress through mild, moderate and severe stages and eventually to cancer. About one in seven of the moderate cases of dysplasia will progress to cancer, and as many as 83% of cases with severe dysplasia have been reported to progress to cancer, depending on the types of cells involved. However, removal of mild and moderate dysplasias greatly reduces the development of cancer. In the lung, removal of dysplastic cells not only greatly reduces the formation of cancerous cells, but in some cases pulmonary tissue will return to a normal morphology.

In general, the earlier cancers are detected, the better the prognosis is for patient survival. If breast cancer is detected early when it is still localized to a single mass, the five-year survival rate is more than 96%. When it has spread to a distant location, the five-year survival rate is less than 20%. For lung cancer, when it is detected as a single mass the 5-year survival is more than 46%. When it has spread, the five-year survival is less than 14%. For cervical cancer, additional improvement in survival occurs when pre-cancerous changes are found and treated before developing into a more severe stage (Boring and Squires 1993, CA Cancer J Clin 43:7-26 and Ferguson 1990, Hematol Oncol Clin N Am 4:1053-1168).

Lung carcinoma is presently the leading cause of cancer mortality among men and women in the United States (Wingo et al. 1995, CA Clinical J Clin 45.8-30). In 1997, there were an estimated 160,000 deaths from lung cancer, accounting for 12% of all cancer deaths in U.S. men and 2% in U.S. women (Boring & Squires 1993, supra). Lung cancer is also one of the most lethal types of cancer, as reflected in a five-year survival rate of only 14%. The poor prognosis for lung cancer patients, relative to other types of human cancer, is due largely to the lack of effective early detection methods. At the time of clinical (symptomatic) presentation, over two thirds of all patients have regional nodule involvement or distant metastases, both of which are usually incurable. In studies of patients with localized (Stage 0 or 1) lung cancer, however, 5-year survival rates have ranged from 40% to 70% (Boring & Squires, 1993, supra; Ferguson, 1990, supra).

Historically, the only diagnostic tests used to detect lung cancer before symptoms occur have been sputum cytology and chest radiography. As a consequence, the efficacy of these tests as mass screening tools has been extensively evaluated in studies over the past several decades. Both tests detect presymptomatic, earlier-stage carcinoma, particularly carcinoma of squamous cells.

Improvements in screening methods have largely centered around improving the utility of sputum cytology through technologic advances in microscopy. Sputum cytology requires a visual examination of a cell sample during which cell size, shape, organization, and a ratio between the size of the cell's nucleus and cytoplasm is used to determine the cell's morphology. Because this assessment of cell morphology requires a visual inspection and classification, the technique requires a significant amount of expertise on behalf of the clinical observer. Various investigations have been conducted with results suggesting that computer-assisted, high resolution image analysis enables detection of subvisual changes in visually normal nuclei associated with several tissue types (Montag et al. 1991, Anal Quant Cytol Histol 13:159-167; Haroske et al. 1988, Arch Geschwulstforsch, 58:159-168; Hutchinson et al. 1992, Anal Quant Cytol Estol 4:330-334). Computer-assisted analysis of DNA distribution in cell samples provided 74% correct morphological classification of nuclei without human review of the material and without the need for visually abnormal nuclei being present when compared with standard cytological testing.

The morphologic assessment of cytological specimens has also improved due to advances in the understanding of lung tumor pathology. Much of this work has centered on the identification of "biomarkers." Biomarkers refer to a wide range of progressive phenotypic and genetic abnormalities of the respiratory mucosa which may be used in determining the potential for bronchial epithelium to fully transform into a malignant tumor. Markers have been broadly classified as morphological changes, immuno/histochemical markers for differentially expressed proteins, markers for genomic instability, markers of epigenetic change (e.g., abnormal methylation), and gene mutations (Hirsh et al. 1997, Lung Cancer 17:163-174).

The expression levels of these markers are now being evaluated in dysplastic and neoplastic cyto/histological tissue samples collected from high risk populations. Among those specimens currently being targeted for exploratory marker analysis is sputum. Interest in sputum samples for biomarker research has been generated from the long-held belief that exfoliated cells recovered in sputum may be the earliest possible indication of an incipient carcinoma, since lung cancer most frequently develops in the bronchial epithelium. Through application of sophisticated molecular genetic techniques (e.g., PCR-based assays), studies are providing evidence that selected biomarkers can be detected in sputum (Mao et al. 1994, Cancer Res 54:1634-1637; Mao et al. 1994, Proc Natl Acad Sci USA 91:9871-9875; Sidransky 1995, J Natl Cancer Inst 87:1201-1202; Tockman et al. 1988, J Clin Oncol, 11: 1685-1693; Tockman et al. 1994, Chest, 106:385s-390s).

Commercially available cancer screening or detection services rely on tests based on cytomorphological diagnosis by trained clinicians who look at each sample and determine the extent and identity of abnormal cell types. This process is not only expensive and time-consuming, it also introduces human judgement and therefore error into the procedure. Recently, a method has been developed for detecting cancerous cells of the lung through use of 5, 10, 15, 20-tetrakis (carboxyphenyl)-porphine (TCPP) (U.S. Pat. No. 5,162,231 to Cole et al). This method relies on the propensity of cancerous cells to accumulate TCPP from their environment in a greater amount than non-cancerous cells. Upon incubation of a cell sample for 6-24 hours with 200 μg/ml TCPP, the TCPP entered cells and bound to the perinuclear membrane and mitochondria of neoplastic cells. TCPP fluoresces under ultraviolet light, and cancerous cells may thereby be diagnosed solely by the intensity of fluorescence, without reference to morphology. The extension of the use of this compound to identifying pre-cancerous tissue conditions (e.g., dysplastic cells) would permit screening in high risk populations to identify those individuals whose tissues are progressing toward invasive cancer conditions, and thereby facilitate catching the cancer or dysplasia at the most treatable stage. The desirable characteristics of such a screening method would be a procedure that is rapid, inexpensive, and requires a minimum of technical expertise.

For the foregoing reasons, there is a need for a technique and methodology for detecting dysplastic cells in their earliest stages. In addition, there is a need for a technique that can provide highly reliable diagnostic results objectively and that does not rely on the subjective analysis of the clinician performing the diagnosis.

SUMMARY OF THE INVENTION

One embodiment of the present invention provides for a method of determining if a sputum sample contains dysplastic or carcinomic cells by obtaining a sputum sample containing cells. The sputum sample is labeled with TCPP to stain cells suspected to be dysplastic or carcinomic. An imager focuses on the plasma membrane of one or more cells suspected to be dysplastic or carcinomic and emission at about 655 nm+/−30 nm, if present, is detected for TCPP labeled cells of the sputum sample after focusing on the plasma membrane of the cells of the sputum sample. Photon flux for each pixel of a sensor is measured to obtain a value for the imaged cell. The measured value is scored to determine if a cell is cancerous or dysplastic.

Another embodiment provides for a method of determining if a biological sample of cells contains dysplastic or carcinomic cell by obtaining a biological sample suspected of containing dysplastic or carcinomic cells. The biological sample is labeled with TCPP. The sample is excited with an excitation wavelength of light of about 475 nm+/−30 nm. An imager is focused on the plasma member of one or more cells suspected of containing dysplastic or carcinomic cells to obtain an image. Emission at about 655 nm+/−30 nm if present is detected from TCPP labeled cells after focusing on the plasma membrane of one or more cells of the biological sample suspected of containing dysplastic or carcinomic cells. Photon flux is measured for each pixel of the sensor to obtain a value for the imaged cell. The measured value is scored to determine if a cell is cancerous or dysplastic.

Yet another embodiment provides a computer readable medium for enabling a computer to characterize a sputum sample, the computer readable medium comprising software instructions or code for enabling the computer to perform predetermined operations. The predetermined operation steps include exciting a sputum sample labeled with TCPP with an excitation wavelength of light of about 475 nm+/−30 nm; detecting within the labeled sputum sample emission at about 560 nm+/−30 nm from cells identified to be macrophages; focusing an imager on the plasma membrane of one or more cells suspected to be dysplastic or carcinomic; detecting emission at about 655 nm+/−30 nm if present for TCPP labeled cells of the sputum sample after focusing on the plasma membrane of the cells of the sputum sample; measuring photon flux for each pixel of a sensor to obtain a measured value for the imaged cell; and scoring the measured value to determine if a cell is cancerous or dysplastic.

In a preferred embodiment the TCPP is Meso Tetra (4-Carboxyphenyl) Porphine. In another embodiment the excitation wavelength is about 475 nm+/−5 nm. In yet another embodiment the emission of macrophages is about 560 nm+/−5 nm. In yet another embodiment the imager is a fluorescent microscope. In yet another embodiment the emission of TCPP labeled cells is about 655 nm+/−5 nm. In yet another embodiment the sensor is a CCD camera. In yet another embodiment the scoring further comprises comparing the measured value to a database of stored values for cancerous, dysplastic and non-cancerous cells to assigning a score based upon the results of the comparison. In yet another embodiment the sputum sample is from a human.

One aspect of the present invention provides for labeling biological samples with Meso Tetra (4-Carboxyphenyl) Porphine or 5, 10, 15, 20 tetrakis (4-carboxyphenyl) porphine defined herein as "TCPP" for the detection of cancerous and precancerous cells.

Another aspect of the present inventions provides for using TCPP to detect cancerous cells in sputum since TCPP will bind preferentially with cancerous and precancerous cells.

Another aspect of the present invention provides a system and method to verify and quantify the spectral signature of TCPP optically, and/or quantify the photon emission rates of TCPP when used as a labeling compound.

Another aspect of the present invention provides for analyzing TCPP labeled samples using a fluorescent system equipped with a tuneable optical filter and Change Coupled Device (CCD).

Additional objects and advantages of the present invention will be apparent in the following detailed description read in conjunction with the accompanying drawing figures.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
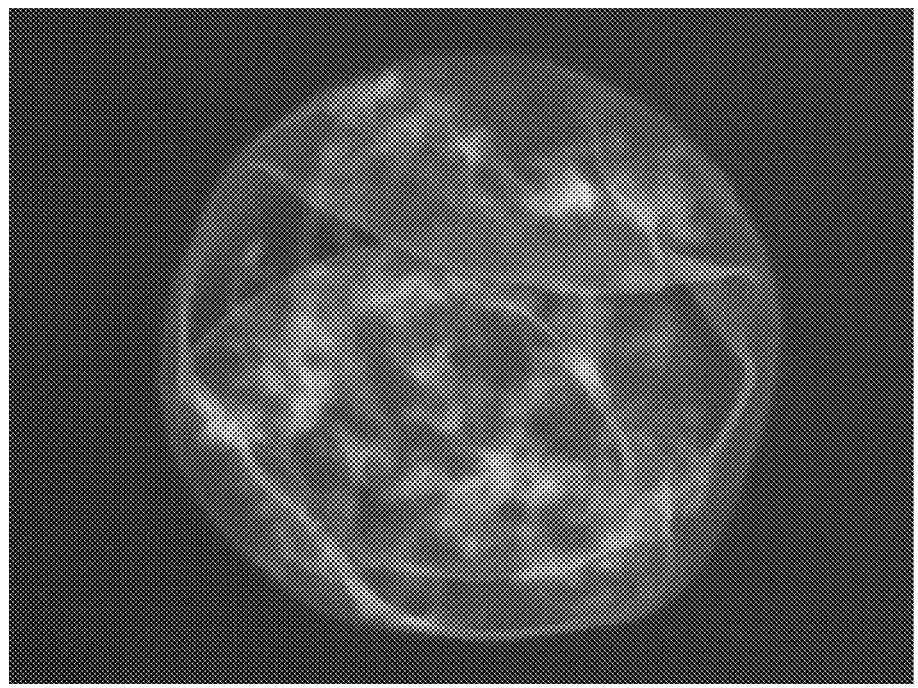
FIG. 1 illustrates a reconstructed 21 layer image of a cell labeled with TCPP.

As used herein "a" means one or more.

As used herein "CCD" means Charge Coupled Device.

As used herein sample "a biological sample" or "sample" or "specimen" refers to a whole organism or a subset of its tissue, cells or components parts (body fluids, including but not limited to blood, mucus, lymphatic fluid, sputum, plasma, ejaculate, mammary duct fluid, cerebrospinal fluid, urine, and fecal stool.

According to one embodiment of the present invention, a system and method for determining the amount of photon emission from TCPP bound to a cell of interest thought to be cancerous relative to the amount of photon emission from TCPP from non-cancerous cells is provided. Since we are determining relative amounts of fluorescence, with all the cells in the same environment, we are not limited to the actual quantum yields of the individual fluorophores. One embodiment of the present invention provides for determination of photon emission from specimens with Equation 1 (Eq. 1).

$$\Phi_R = \frac{\Lambda_{TCPP\ pos}}{\Lambda_{TCPP\ neg}} \qquad \text{Eq. 1}$$

Where $\Lambda_{TCPP\ pos}$ is the number of photons emitted per second photon flux per unit area of cell membrane for a cancerous cell and $\Lambda_{TCPP\ neg}$ is the number of photons emitted per second per unit area for a normal cell.

According to one embodiment of the present invention, TCPP adheres preferentially to the plasma membrane of a cell and even more preferentially to a cancerous cell. TCPP binds to a cancerous cell or precancerous cell preferentially as compared to non-cancerous cell. It has been observed that cancerous cells have an abnormally high concentration of low density lipoproteins on their plasma membranes thereby giving rise to the quantifiably higher fluorescence emission from TCPP at a wavelength between about 200-900 nm, preferably between about 420-720 nm more preferably between about 600-700 nm more preferably about 655 nm+/−30 nm. The difference in spectral signatures from cells labeled with TCPP versus those without TCPP label have a pronounced spectral peak in the between 420 nm-720 nm region. In addition, a filter for example a Liquid Crystal Tunable Filter (LCTF) within the system facilitates demonstration of not only the location of where TCPP is binding and/or concentrating in regards to the cell structure, but also allows quantification of the photon emission in the region of reference relative to the rest of the fluorescent signature from the cell or other that is not due to TCPP.

Image Capture Device

One embodiment of the present invention provides for a sensor, for example, a Charge Couple Device "CCD" sensor, for example a CCD camera but not limited thereto to capture an image of a TCPP stained specimen. In one embodiment a CCD is semiconductor device made from an epitaxial layer of doped silicon grown on a silicon substrate. By creating separated pixels connected to a shift register, the image focused on a two-dimensional array of these pixels can be stored electronically. A pixel may be described by its size and the number of electrons it can hold. For one application herein, the CCD sensor is used to determine the number of photons impacting specific pixels in the array. This is accomplished by measuring the voltage developed across the capacitive junction of each pixel over a given time. The charge that creates the difference in potential is directly related to the number of photons impacting each pixel quantum mechanically. For each photon that is absorbed by the doped silicon, a specific number of electrons are liberated and excited into the valence levels of the semiconductor. The quantum efficiency of a CCD sensor is represented by a quantum efficiency curve associated with a specific CCD sensor.

A CCD sensor allows the measurement of the number of photons by registering the voltage developed across each pixel junction as read through the serialized output of the shift register, basically a sequence of binary coded hexadecimal values ordered according the sequence in which the shift register outputs the pixel voltages. As each of these values is directly proportional to the number of photons impacting each pixel during a period of time, these values can be correlated to the photon emission flux of the source of the photons.

An extraordinary amount of information can be gathered concerning the composition of cellular structures by isolating the specific wavelengths of emitted photons that are being emitted by specific structures of the cell or by probes or labeling compounds such as TCPP that bind to a cell or portion thereof. For example, if normal auto-fluorescence occurs in the 560 nm range, and a certain defective structure fluoresces in the 590 nm range, the size, shape, and other aspects of the defective structure can be seen by filtering out all the wavelengths other than the 590 nm wavelength and then using the selected wavelength output to create the image on the CCD sensor. The actual number of photons per unit area of cell structure per unit time can then be determined by measuring the voltages developed per unit time per pixel and correlating that value to the magnification of the optical system and the attenuation of the individual components.

Porphyrin Fluorescence Basics

Porphyrins are planar aromatic macromolecules consisting of four pyrole rings joined by four methane bridges. They are natural occurring compounds that are found in plants, hemoglobin, and come in myriads of forms. A porphyrin as used herein is a probe or labeling compound.

When illuminated with light of the correct wavelength, most proteins will produce fluorescent photons with wavelengths in the about 490 nm to 600 nm range. Porphyrins, however, have quite the varied absorption and emission spectra.

Figure 4:
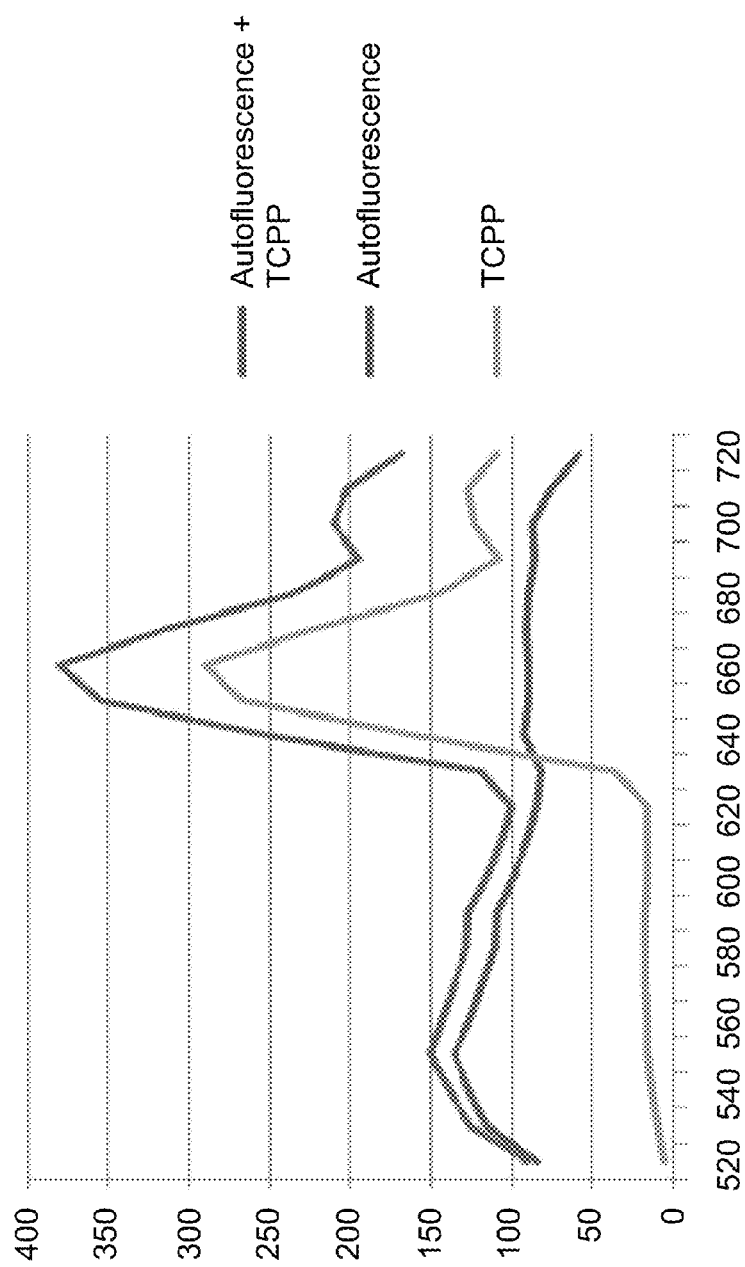
FIG. 4 illustrates plot of spectral signatures from FIG. 1.

By labeling cells with porphyrins (for example TCPP), fluorescence microscopy allows the imaging of cell structures that are highlighted by the labeling compound (see FIG. 1). Tailoring the labeling compound to attach to specific targets in the cell gives the ability to highlight specific cell structures. Referring now to FIG. 1, structures within the cell exhibit auto fluorescence in the green wavelength while the plasma membrane fluoresces in the red wavelength when the cell is illuminated with an excitation wavelength of about 465 nm+/−30 nm. FIG. 4 illustrates the spectral plot obtained from a spectral scan of the image in FIG. 1.

Figure 2:
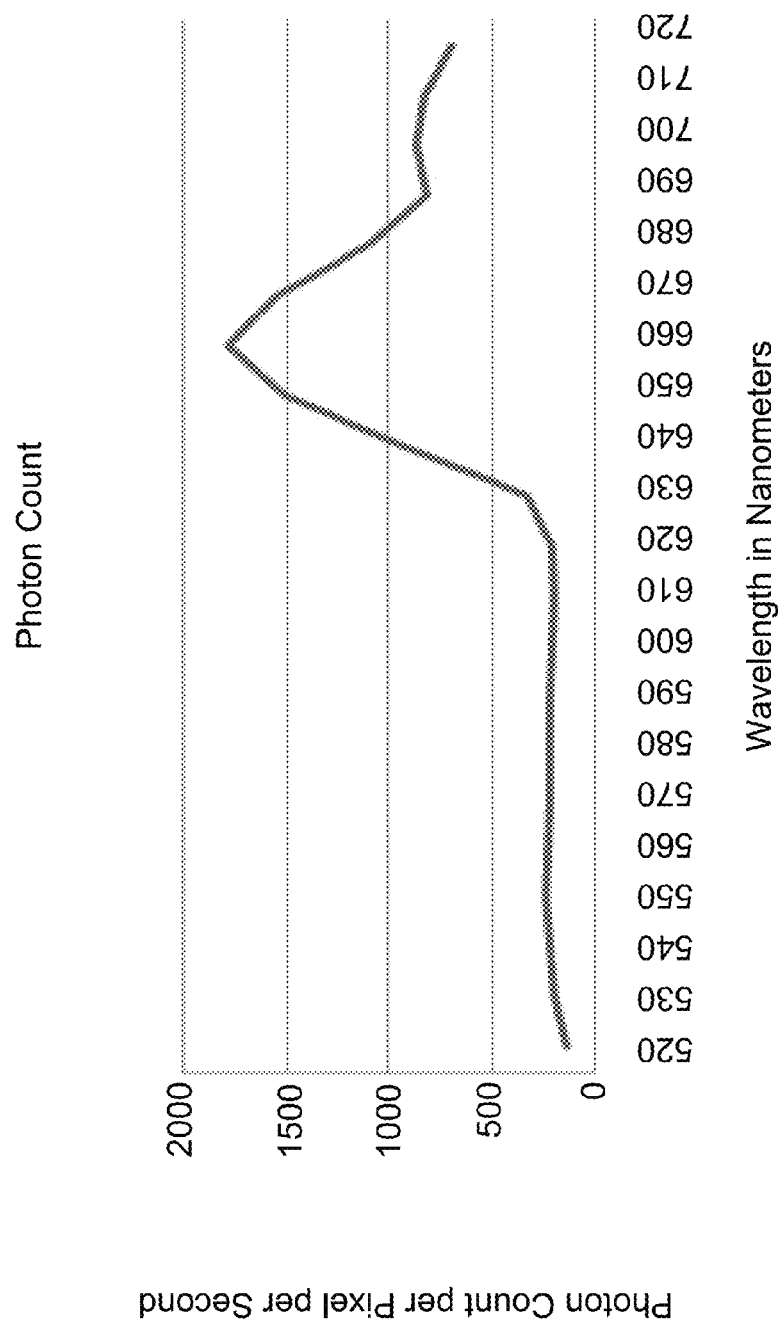
FIG. 2 illustrates fluorescence optical spectrum of TCPP labeled plasma membrane (non-corrected units).

A chart illustrating a fluorescence optical spectrum of TCPP labeled Plasma Membrane of a cell from a biological specimen is shown in FIG. 2 according to one embodiment of the present invention.

Experimental Protocol

According to one embodiment of the present invention, a biological specimen, for example a sputum sample is processed using a thin prep protocol onto a microscope slide. The sputum sample is fixed in a methanol based solution which has been demonstrated to be less corrosive to the plasma membrane of a cell from a cell population of interest. Minimizing corrosive effects to the plasma membrane is important as the TCPP is shown to localize on the plasma membrane of the cell surface. The cells are processed to separate the cells from the mucous and cell fragments. Each prepared slide contains a monolayer of the sputum cells. After preparing the slides, the labeling reagent TCPP is dissolved in concentrations between 0.05 µg/ml-4.0 µg/ml in an aqueous alcohol containing between 50% and 90% isopropanol alcohol solution. The pH is adjusted with sodium Bicarbonate to a pH between 6.0 and 10.5. The slide is immersed in the TCPP labeling solution, rinsed, air-dried, and a cover-slip is placed on top. (See for example U.S. Pat. No. 7,670,799 to Garwin).

Imager

An imager such as a scope, for example, a microscope, preferably a Fluorescent Microscope is utilized by the system according to one embodiment of the present invention.

Excitation Source

A light source, for example, a Mercury Vapor Lamp or preferably a laser which may be tuned to user specified wavelengths is further utilized by the system according to one embodiment of the present invention.

Optics

Fluorescence optics cube with a blue visible frequency notch filter. Fluorescent light from the sample on a specimen platform, for example, a slide then passes through a beam splitter to the microscope objective and on to a CCD camera in a preferred embodiment. In addition the system may also comprise a processor, a database and computer readable instructions for obtaining a score from an image and producing a report based upon the score.

TCPP has a pronounced molar absorption coefficient around 400 nm, called the Soret band. Although very efficient in this region, photo-bleaching occurs. Therefore, a region of the spectrum where the absorption by TCPP is not so efficient may be selected, thereby eliminating most of the photo-bleaching and extending the fluorescent lifetimes for which the samples are viable.

In one embodiment, a region in the blue spectrum 475 nm+/−30 nm was the selected excitation wavelength. A band pass filter centered on about 475 nm was employed. A fluorescent optical cube also contained a dichroic beam splitter that has a fairly flat optical transmission frequency response in the visible above 500 nm with second pronounced transmission peak below that centered around 400 nm allowing any of the light corresponding to the Soret band that happens to get through the excitation filter to pass through and not be reflected to the sample.

Image Capture and Method for Obtaining Image

To gather our data an image capture system having a detector capable of quantifying emission of photons from a TCPP labeled cell across light spectrum from about 350 nm to about 800 nm was employed according to one embodiment of the present invention. The system comprises an imager as a scope for example a microscope more preferably a fluorescent microscope. An image sensor and capture device which may be automated for data acquisition for optimizing emission capture of an image. The image capture device may attach directly to an imager such as a fluorescent microscope. A filter, for example, a Liquid Crystal Tunable Filter, (LCTF) but not limited thereto allows the capture of images from different optical frequencies, and the measurement of the emission at those different frequencies. However, other filters (customized or off the shelf) may be utilized and other filtering techniques may be utilized and is not limited to LCTF. In addition, a light source, for example a mercury vapor lamp or more preferably a laser which may be tuned to a user specified wavelengths is useful for illuminating the specimen. In one example, a mercury vapor lamp having luminous efficacy 30 lm/W luminous flux 3000 h luminous intensity 300 cd luminance 17000 cd/cm2 and known spectral characteristics was utilized in the system according to one embodiment of the present invention.

Figure 3:
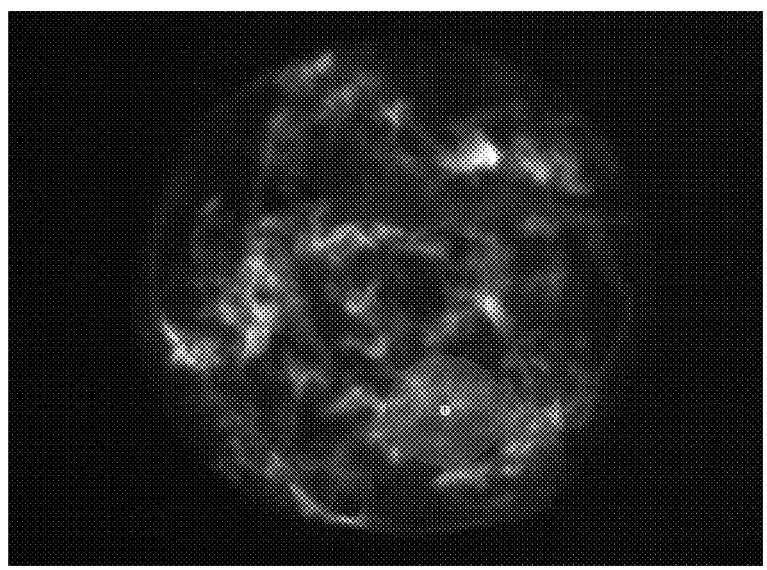
FIG. 3 illustrates fluorescent image of cells with area of interested marked in red.

Referring now to FIG. 1 is a cell labeled or stained with TCPP according to one embodiment of the present invention. The image is reconstructed from multiple images acquired over at designated wavelengths over a user defined spectrum and the resulting images are recombined. For example 21 layers of an image with each layer acquired at a different wavelength were obtained from the cell labeled with TCPP. The autofluorescence of the cells is detected in the green channel 560+/−30 nm and the fluorescence of the TCPP labeling compound on the cell is detected in the red channel 660+/−30 nm. One embodiment of the system and method of the present invention provides for the isolation of specific frequencies for imaging of the cell and measuring frequencies by tuning the LCTF. By tuning the LCTF to different frequencies during imaging, the system permits information to be gathered and analyzed over a broad spectrum. Then, after capturing each image for a specific wavelength range, the specific optical spectra of interest may be extracted. The image with spectral enhancements to highlight specific features from the image is displayed. Then a grey scale image is measured with the LCTF tuned to the appropriate frequency, see for example FIG. 3. The photon flux is measured from a specified cell structure(s) in the image (see for example the red circle with bulls-eye positioned over the area of interest). The determination of a relative threshold emission value for determining whether a cell is cancerous or not is then determined. This also allows the separation of emissions by different cell structures and quantifying the emissions to produce a value. In addition one or more of the following features from the image and or cell of interest may also be useful in scoring: ROI Number, Cube ID, Avg Signal (counts), Avg Signal (scaled counts/s), Avg Signal, (x10^6Photons/cm2/s), Avg Signal (OD), Std Deviation Counts, Std Deviation Scaled Counts, Std Deviation (x10^6Photons/cm2/s), Std Deviation (OD), Total Signal Counts, Total Signal Scaled Counts (x10^6Photons/cm2/s), Total Signal (OD), Max Signal Counts, Max Signal Scaled Counts, Max Signal (x10^6Photons/cm2/s), Max Signal (OD), Area Pixels, Area (um)2, Major Axis, Minor Axis, x location, y location, Spectrum ID, Cube Time Stamp, Cube, Visual Fluorescence, Cell Morphology (size, shape, not limited to type, characteristics), Spectral Signature (TCPP), Background Fluoresence, Signal/Background Ratio, Std Deviation, signal/Background Ratio, Fluorescence (Auto, TCPP)), Capture Image Cube Narrow Band Width, Capture Image Cube Full Spectrum.

In one embodiment of the present invention the value produced by the scoring is correlated to a cancerous cell or non-cancerous cell to determine the health of a patient.

The system permits the separation of an image based upon specific wavelengths as well as selecting specific regions in that image in order to measure the signal from the CCD sensor, and then export the spectral data for analysis.

Data: Spectral Signature of TCPP

Figure 5:
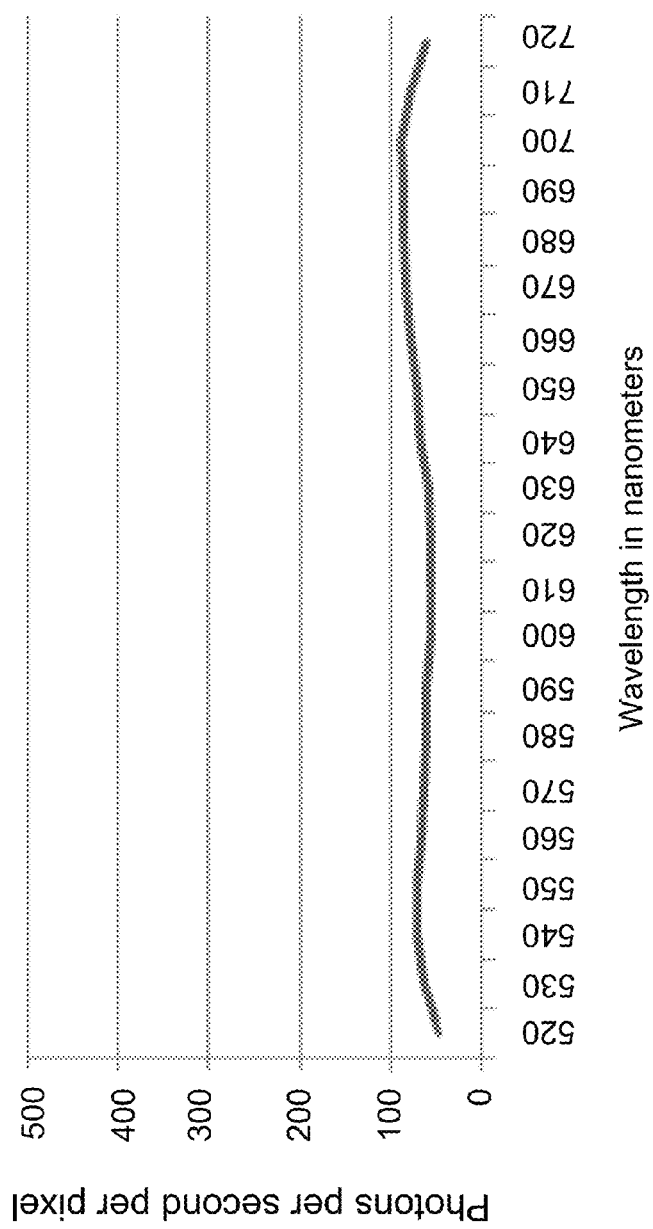
FIG. 5 illustrates plot of spectral signature of auto-fluorescence from the blue highlighted region of FIG. 6.
Figure 6:
FIG. 6 illustrates cells imaged for auto-fluorescence and labeled with TCPP.

Referring now to FIG. 6, the image is from a sample of lung sputum that was placed on a microscope slide according to the above listed procedure. The slide was illuminated with light having an about 475 nm wavelength from the mercury vapor source filtered through a band-pass filter a long pass beam splitter, approximately 500 nm cutoff. The image was taken before the labeling procedure in order to demonstrate the spectral signature of TCPP relative to the normal auto-fluorescence of the cell structures. An area highlighted in blue, of FIG. 6, was analyzed using color and the graph, of FIG. 5, shows the spectral components of the image. Referring now to FIG. 5, a plot of a spectral signature or auto-fluorescence from the blue highlighted region in FIG. 6 is illustrated.

Figure 7:
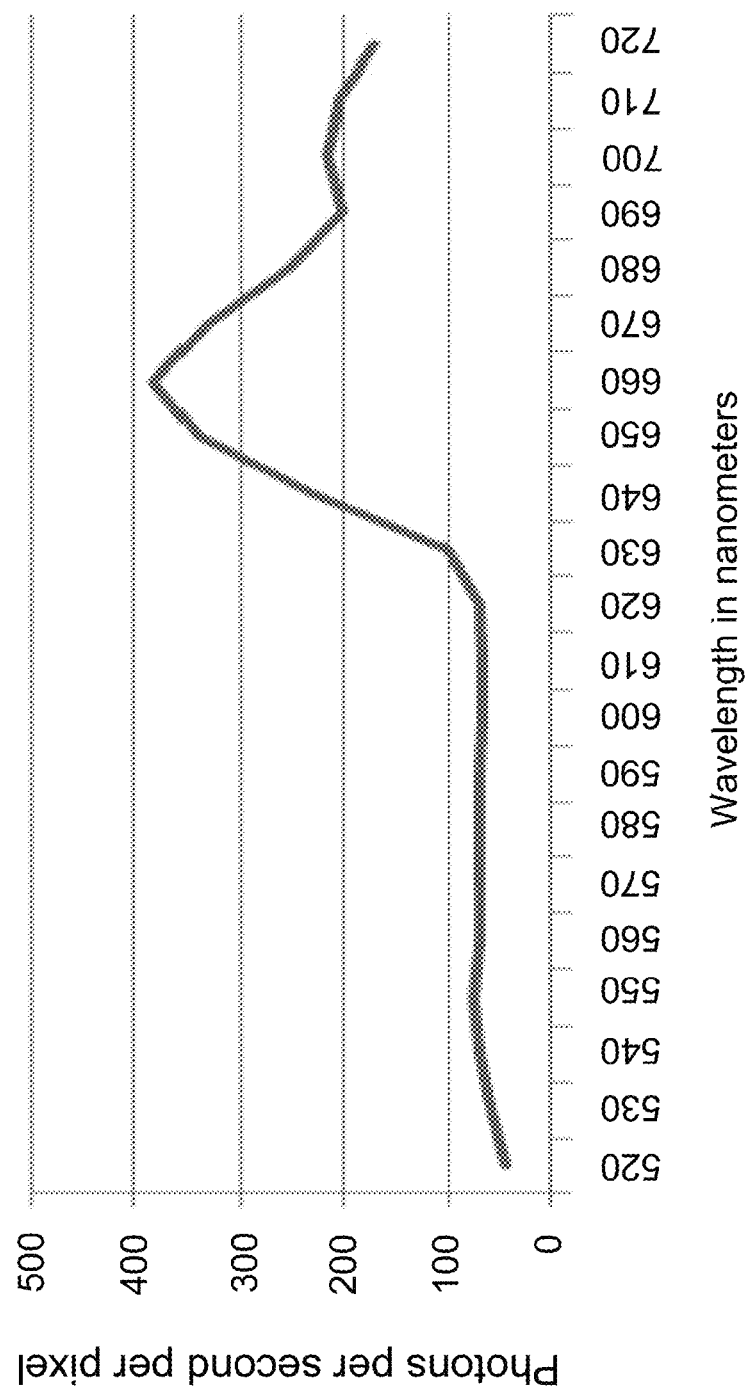
FIG. 7 illustrates plot for TCPP labeled cell membrane from the blue highlighted region of FIG. 6.

The specimen of FIG. 6 was then labeled with TCPP and re-imaged. The area highlighted in blue, of FIG. 6, was imaged with the CCD sensor and analyzed. The plot in FIG. 7 shows the fluorescent spectral output of TCPP (the green line) from the blue highlighted region of FIG. 6 as imaged. The photons per second per pixel are in arbitrary units.

The scales were set to the same value in order to demonstrate the spectral signature of the staining compound. The peak around 660 nm is due to the TCPP staining compound.

Data: Location of TCPP in Cell Structures

Another feature of the present invention illustrates that the TCPP compound localizes to the plasma membrane of a cell. By separating the images by spectral emission it can be shown that the emission of the TCPP labeling compound is emitted exclusively from the plasma membrane. The microscope can be focused on the structures that are emitting at specific wavelengths in the visible range. Images of (either internal or external) features of the fluorescing cell structures are obtained. Images of a cell, portions thereof and cellular structures emitting photons at different wavelengths are illustrated in FIG. 1.

Figure 8:
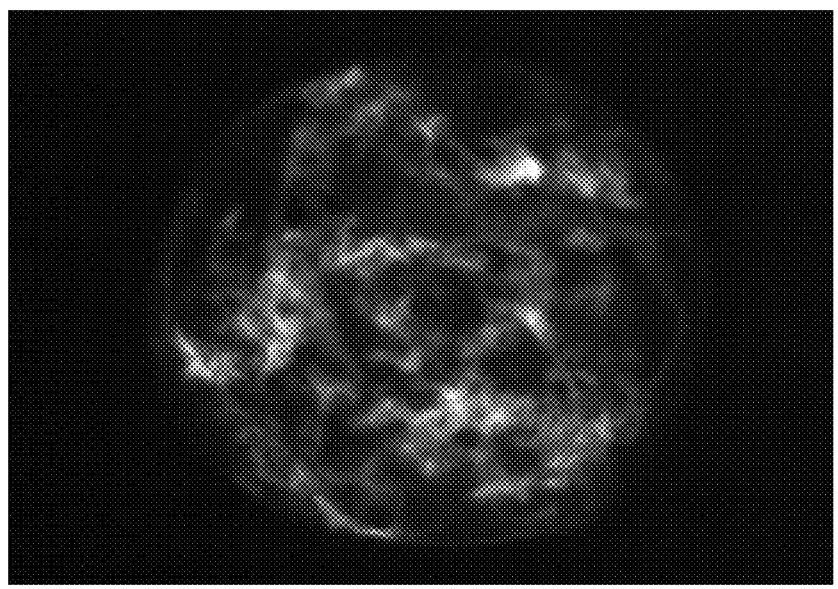
FIG. 8 illustrates 530 nm layer focused at 660 nm.

FIG. 8 is a grayscale image taken with the LCTF tuned to about 530 nm. The image shows internal structures that were located below the layer that emitted the TCPP signature. FIG. 8 was taken with the focus of the microscope set on cell structures that were seen with the LCTF set to 660 nm. In order to bring this image into focus the field of focus had to be physically lowered. The image that resulted (not shown) from lowering the field of focus demonstrated more definition and was in better focus and the plasma membrane is better defined than FIG. 8. This is due to the fact that some of the light being emitted from the lower cell structures is occluded by the plasma membrane.

Figure 9:
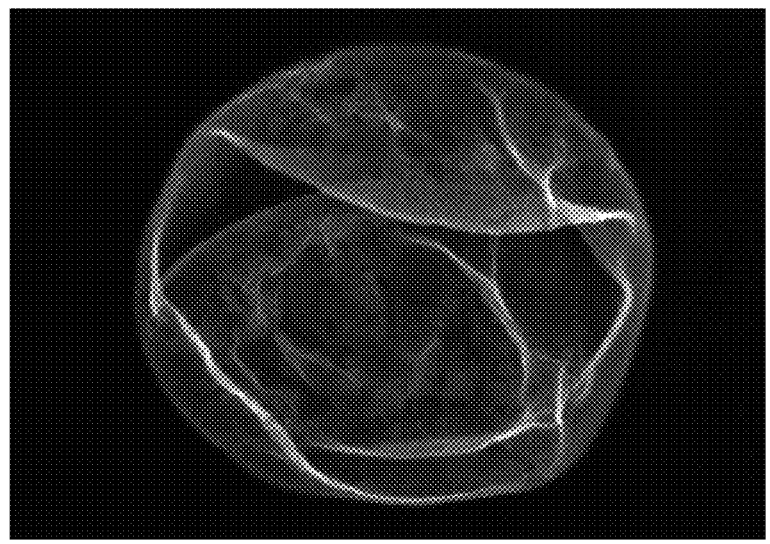
FIG. 9 illustrates 660 nm layer focused at 660 nm.

The image in FIG. 9 was obtained with the LCTF tuned to 660 nm. The field of focus was raised relative to the focal field for the 530 nm image. As the excitation light was coming from above the slide, combined with the fact that only the exposed surface of the cells were subjected to the staining compound during the staining process, the images support the premise that TCPP adheres only to surface features and does not migrate into internal cell structures. When this is taken into consideration with FIG. 9, it demonstrates that the objects emitting a 530 nm signature were located physically below those emitting an about 660 nm signature. The plasma membrane in FIG. 9 is focused.

Data: Measurement of the Fluorescing Flux of a Cancer Cell Labeled with TCPP

Determination of the photon flux from the fluorescing cell is based on the saturation level and quantum efficiency of the CCD sensor. The basis for the values calculated is as follows:

According to one embodiment of the present invention, the photons emitted by the fluorescing structures pass through 12 mediums before impacting the CCD. These consist of the slide cover, the optics in the objective, the optics cube, the beam splitter for the microscope, the LCTF, and the air gaps between each. We have taken into consideration the transmission coefficients for each of the mediums at the relevant wavelengths, along with the wavelength dependant attenuation of the LCTF and quantum efficiency of the CCD in order to arrive at a value for the number of photons emitted per second arriving at each pixel of the CCD. Of course there is a bandwidth consideration due to the bandwidth of the LCTF. Each of the bandwidths in question have a specification of 20 nm full width at half max (FWHM).

The equation below gives the basic form of the expression used.

$$(PCCCD)/[(0.99)(MO)(OC)(LCTF)(QECCD)] = \text{photon flux from cell per pixel}$$

Where PCCCD is the photon count from the CCD, MO is the attenuation attributed to the microscope optics, OC is the attenuation of the optics in the fluorescent optics cube, LCTF is the attenuation due to the liquid crystal tunable filter, and QECCD is the quantum efficiency of the CCD chip. The 0.99 term is to account for the absorption of photons in the slide cover and the scattering and other losses due to the air gaps and Fresnel reflections.

All the data was collected using a 20× objective with a numerical aperture of 0.7. This allows the data to be correlated to the actual size of the emission area of the cell structure. The data analysis allows the measurement of the photon count over specified areas of the image. In this particular case, the image capture device for example a CCD which may consists of a 1392×1040 pixel array. Determining the actual dimensions of the measured area is simply a matter of geometry.

Once an image is captured the relevant grayscale layer is isolated and a region of interest is specified. The charge on each element of the CCD sensor is acquired. Based upon the charge, a value for the number of photons absorbed by that element at that wavelength is determined. Using this value, the actual number of photons emitted by the fluorescing source can be estimated with the above relationship. The value is scored against controls and a score is assigned. The assigned score determines whether the cell screened is cancerous or non-cancerous.

The information for the specified region in terms of the number of pixels in the specified region, the total number of counts in the specified region, the number of counts from the pixel with the highest value and the standard deviation for the frequency distribution is calculated.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. For example, wavelengths are provided as about a specific wavelength and about specified ranges of wavelengths. It should be understood that some embodiments permit +/−30 nm flux. Also specific examples are provided that relate to sputum samples but biological samples may be of any type and obtained by different means as is identified in U.S. Pat. No. 6,316,215 to Adair. The entire disclosures of all references, applications, patents, and publications cited above are hereby incorporated by reference.

The present invention has been described in terms of preferred embodiments, however, it will be appreciated that various modifications and improvements may be made to the described embodiments without departing from the scope of the invention. The entire disclosures of all references, applications, patents, and publications cited above and/or in the attachments, and of the corresponding application(s), are hereby incorporated by reference.

What is claimed is:

1. A method of determining if a biological sample of cells contains dysplastic or carcinomic cells the method comprising:

obtaining a biological sample suspected of containing dysplastic or carcinomic cells from human sputum from a patient suspected of having lung cancer;

labeling the biological sample with between about 0.05-1.0 μg/ml of Meso Tetra (4-Carboxyphenyl) Porphine (TCPP) in an aqueous alcohol of between 50% and 90% isopropanol alcohol solution at a pH of between 6.0 and 10.5 to stain cells suspected to be dysplastic or carcinomic;

exciting the sample with an excitation wavelength from a light source having a controlled emission rate for a wavelength of light limited to 475 nm+/−30 nm;

focusing an imager on the plasma membrane of i) one or more cells suspected of containing dysplastic or carcinomic cells and ii) normal cells to capture an image of i) and ii) at a sensor having pixels capable of quantifying the photon flux at any given pixel on the sensor wherein the sensor comprises a CCD and wherein the imager comprises a fluorescent microscope;

detecting at the sensor emission limited to 655 nm+/−30 nm if present from TCPP-labeled cells after focusing on the plasma membrane of i) one or more cells suspected of containing dysplastic or carcinomic cells and ii) normal cell one or more cells of the biological sample suspected of containing dysplastic or carcinomic cells;

measuring photon flux at each pixel of the sensor to obtain a quantitative value for the imaged cells; and automatically scoring with an appropriately-programmed processor whereby the measured quantitative value to determine if a cell is cancerous or dysplastic based upon a preferential binding of TCPP to the plasma membrane of a cancerous or dysplastic cell as compared to the plasma membrane of a non-cancerous cell.

2. The method of claim 1 further comprising:
detecting emission from cells identified to be cells of interest at 560 nm+/−30 nm.

3. The method of claim 1 wherein the excitation wavelength is 475 nm+/−5 nm.

4. The method of claim 1 wherein emission of macrophages is 560 nm+/−5 nm.

5. The method of claim 1 wherein the emission of TCPP labeled cells is 655 nm+/−5 nm.

6. The method of claim 1 wherein the scoring further comprises comparing via the programmed processor the measured value to a database of stored values for cancerous, dysplastic and non-cancerous cells to assigning a score based upon the results of the comparison.

* * * * *